United States Patent
Marchionna et al.

(10) Patent No.: US 6,897,345 B2
(45) Date of Patent: May 24, 2005

(54) PROCESS FOR THE PRODUCTION OF HYDROCARBONS WITH A HIGH OCTANE NUMBER STARTING FROM MIXTURES OF N-BUTANE/ISOBUTANE SUCH AS FIELD BUTANES

(75) Inventors: Mario Marchionna, Milan (IT); Marco Di Girolamo, San Donato Milanese (IT); Domenico Sanfilippo, Paullo (IT); Alberto Paggini, Spino D'Adda (IT)

(73) Assignee: Snamprogetti S.p.A., San Donato Milanese (IT)

( * ) Notice: Subject to any disclaimer, the term of this patent is extended or adjusted under 35 U.S.C. 154(b) by 0 days.

(21) Appl. No.: 10/420,895

(22) Filed: Apr. 23, 2003

(65) Prior Publication Data

US 2004/0010171 A1 Jan. 15, 2004

Related U.S. Application Data

(62) Division of application No. 09/986,562, filed on Nov. 9, 2001, now abandoned.

(30) Foreign Application Priority Data

Nov. 9, 2000 (IT) ..................... MI2000A2417

(51) Int. Cl.$^7$ ................. C07C 2/54; C07C 2/04
(52) U.S. Cl. ................. 585/315; 585/314; 585/324; 585/329; 585/331; 585/332
(58) Field of Search ................. 585/315, 314, 585/324, 329, 331, 332

(56) References Cited

U.S. PATENT DOCUMENTS

| | | | |
|---|---|---|---|
| 4,393,250 A | * 7/1983 | Gottlieb et al. | ............. 568/697 |
| 4,523,048 A | 6/1985 | Vora | |
| 4,734,540 A | 3/1988 | Gattuso et al. | |
| 4,761,509 A | 8/1988 | Vora et al. | |
| 4,868,342 A | 9/1989 | Verson | |
| 5,689,015 A | 11/1997 | Hunt et al. | |
| 5,877,372 A | 3/1999 | Evans et al. | |

* cited by examiner

Primary Examiner—Thuan D Dang
(74) Attorney, Agent, or Firm—Oblon, Spivak, McClelland, Maier & Neustadt, P.C.

(57) ABSTRACT

A process is described for the production of hydrocarbons with a high octane number starting from mixtures essentially consisting of n-butane and isobutane (such as for example field butanes) comprising a skeleton isomerization section, a dehydrogenation section of paraffins, a selective hydrogenation section of butadiene, two conversion sections of olefins, in which the isobutene is firstly selectively transformed by means of dimerization and/or etherification, followed by the linear butenes by means of alkylation, in order to obtain, by joining the products of the two conversion sections, a product having excellent motoristic properties (octane number, volatility and distillation curve).

5 Claims, 1 Drawing Sheet

Figure 1:
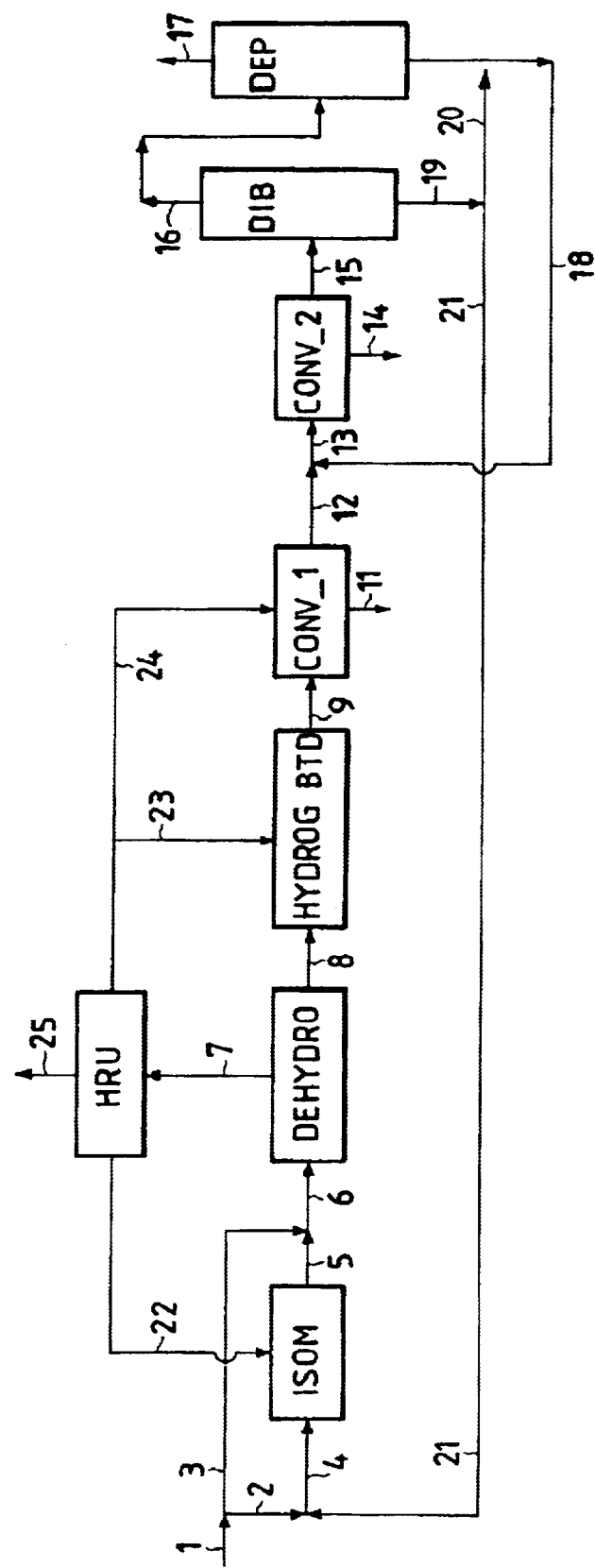

PROCESS FOR THE PRODUCTION OF HYDROCARBONS WITH A HIGH OCTANE NUMBER STARTING FROM MIXTURES OF N-BUTANE/ISOBUTANE SUCH AS FIELD BUTANES

The present invention relates to a process for the production of mixtures of hydrocarbons with a high octane number starting from mixtures of n-butane/isobutane such as for example mixtures of field butanes. According to the process claimed, the mixture essentially consisting of n-butane and isobutane is fed to a dehydrogenation section and the olefins thus obtained are converted (by means of dimerization reactions, and/or optionally also etherification and alkylation reactions) into a mixture having excellent octane properties.

Field butanes (n-butane/isobutane mixtures often in a ratio of about 3/1 but not necessarily) are generally utilized in the synthesis of MTBE in high capacity complexes (300–800,000 t/year) consisting of skeleton isomerization units, dehydrogenation of isobutane and the synthesis of ether.

This consolidated scenario however is now rapidly changing as a result of reformulation process of gasolines which require ever-increasing quantities of purely hydrocarbon products (characterized by the absence of aromatics, olefins, sulfur and with a low volatility and high octane number) and the probable reduction of the MTBE market.

The ban of MTBE from gasolines in California with its likely extension to the rest of the USA and the continual attacks to which ether itself is subjected owing to its presumed environmental impact, have in fact jeopardized its use (and also that of other methyl or ethyl ter-alkyl ethers) in future reformulated gasolines.

This considerable market decrease is causing great difficulties for the existing plants (which may have to vary their production or close) and is also hindering new industrial initiatives for exploiting field butanes as high quality products for gasolines.

As far as modifying existing plants is concerned, the main alternatives to the production of MTBE consist in the manufacturing of hydrocarbon products, still with a high octane number, by means of the dimerization or alkylation of isobutene.

The alkylated and dimerized products of isobutene are in principle ideal compounds for reformulated gasolines, as they satisfy all the requisites required by future environmental regulations owing to their combination of a high octane number with a low volatility and a complete absence of olefins and aromatics.

The introduction of a dimerization section of isobutene, followed by hydrogenation of the olefinic product, instead of etherification, is undoubtedly the simplest solution which however, owing to the fact that there is no methanol contribution, causes a reduction of a third of the production (with the same capacity of the dehydrogenation reactor).

The other possibility of revamping consists in the substitution of the etherification unit with an alkylation unit in which both isobutane and isobutene react to give the alkylated product. In this case, thanks to the activation of the paraffin, the productivity increases and thus also the potential yield of the plant.

Unfortunately the alkylation product between isobutane and isobutene is of a low quality when sulfuric acid is used as alkylation catalyst; the quality obtained using hydrofluoric acid is slightly better but this is generally undesirable for environmental reasons. As far as innovative alkylation systems are concerned (see the paragraph dedicated to alkylation below), either these do not seem suitable for this type of alkylation, or again they produce quite a low quality alkylated product. This means that the alkylation of isobutene should be carried out either only on n-butenes or on mixtures of isobutene/n-butenes.

Also in this latter case, however, the relative concentrations of isobutene with respect to n-butenes must be very low to avoid a negative effect on the process and on the alkylation product (n-butene/isobutene>4).

To conclude, the simple revamping of an MTBE plant by means of the alkylation of isobutene/isobutane does not seem to be particularly attractive to the market.

There is obviously a great interest in producing new reaction schemes which allow the exploitation of field butanes, a problem which has so far remained unsolved.

A new process scheme has now been set up, in which the advantages obtained from the two conversion processes are surprisingly combined to obtain a mixture having excellent motoristic properties.

The process, object of the present invention, for the production of hydrocarbons with a high octane number starting from mixtures essentially consisting of n-butane and isobutane, preferably having an n-butane/isobutene ratio ranging from 1/5 to 5/1, more preferably from 1/1 to 5/1, in particular mixtures of field butanes, is characterized in that it comprises a skeleton isomerization section, a dehydrogenation section of paraffins, a selective hydrogenation section of butadiene, two conversion sections of olefins, in which the isobutene is firstly selectively transformed by means of dimerization and/or etherification, followed by the linear butenes by means of alkylation, in order to obtain, by joining the products of the two conversion sections, a mixture of hydrocarbons having a high octane number.

The process according to the invention preferably comprises the following steps:

a) feeding a part of the mixture essentially consisting of n-butane and isobutane, a stream of hydrogen and a stream consisting of recycled n-butane, to a skeleton isomerization section;

b) joining the product leaving the skeleton isomerization section with the remaining part of the mixture essentially consisting of n-butane and isobutane and sending the mixture thus obtained to a dehydrogenation section of paraffins;

c) sending the stream leaving the dehydrogenation to a selective hydrogenation of butadiene;

d) sending the stream leaving the selective hydrogenation section to a first conversion section in which the isobutene is reacted by means of dimerization and/or etherification, separating the dimerized and/or etherified product from the non-reacted $C_4$ hydrocarbon stream, mainly consisting of isobutane, n-butane and linear butenes, and subjecting said product, only if it has been dimerized, to hydrogenation, obtaining a hydrocarbon stream mainly containing iso-octane;

e) sending the $C_4$ hydrocarbon stream leaving the first conversion section, mainly consisting of isobutane, n-butane and linear butenes, to a second conversion section in which all the linear butenes are reacted by means of alkylation obtaining a stream of saturated hydrocarbons;

f) sending the non-reacted butanes in the second conversion section to a first separation column (deisobutanizing column) from whose head a stream essentially consisting of propane and isobutane is recovered and from whose bottom n-butane is recovered to be recycled to the skeleton isomerization section;

g) sending the stream at the head of the first separation column (deisobutanizing column) to a second separation column (depropanizing column) from whose head the light products are recovered and from whose bottom the isobutane is recovered, which is recycled either preferably to the second conversion section and/or to the first conversion section and/or to the selective hydrogenation section.

In the first conversion section of step (d) the preferred reaction is the dimerization of isobutene.

A further object of the present invention relates to the mixture of hydrocarbons with a high octane number, essentially containing saturated hydrocarbons with from 5 to 16 carbon atoms and in which at least 50% by weight are saturated $C_8$ hydrocarbons, which is obtained by means of the process according to the invention by joining the hydrocarbon stream containing iso-octane produced in the first conversion step with the stream of saturated hydrocarbons produced in the second conversion step.

When the isobutene in the first conversion step is subjected to dimerization, the percentage of saturated $C_8$ hydrocarbons in the mixture of hydrocarbons with a high octane number is at least 60% by weight.

The mixture obtained by joining the products of the two conversion steps has further improved octane properties. Moreover, the alkylation is effected on an olefinic charge containing linear butenes (mainly 2-butenes as explained below) and this serves to maximize the quality of the alkylated product.

Operating in this way, it is possible to obtain a "Superalkylated" product, with excellent octane properties (RON ranging from 97 to 100, MON ranging from 95 to 97), and at the same time, with an equal volume of the dehydrogenation unit, also to obtain very high plant productivities, much higher than in the case of the dimerization of isobutene alone.

Let us now examine in detail the single sections which form the process according to the invention.

Skeleton Isomerization

The skeleton isomerization of n-paraffins is a process which dates back to the thirties', and is therefore now quite consolidated, which uses a bifunctional catalyst with an acid component (alumina) and a dehydrogenating-hydrogenating agent (noble metal). For more specific information in this respect see R. A. Meyers, "Handbook of Petroleum Refining Processes", McGraw-Hill, part. 5.4.

Dehydrogenation

As of today, there are no commercial processes specifically and exclusively designed for the dehydrogenation of field butanes (i.e. of n-butane/isobutane mixtures). This is mainly due to the wide demand on the market for isobutene, which in the past has led producers to preferably attempt to isomerize linear products.

There are numerous processes however which more generally claim the capacity to dehydrogenate light paraffins (typically $C_3$–$C_5$) and which, although so far having been almost exclusively applied to the dehydrogenation of propane and isobutane, can also in principle be applied to the case of n-butane and even more so to the case of n-butane/isobutane mixtures. With respect to the more consolidated dehydrogenation reaction of isobutane to isobutene, the dehydrogenation of n-butane does in fact present greater difficulties, associated with the relative facility with which the subsequent passage relating to the formation of the diolefin (1,3-butadiene), which normally leads to the formation of poly-unsaturated products, aromatics and coke, can take place, thus lowering the yields to linear butenes.

The dehydrogenation reaction is endothermic and is therefore carried out at high temperatures (450–650° C.) whereas the pressure, owing to the increase in the number of moles, has the effect of slowing down the trend and consequently pressures are adopted close to atmospheric values if not in slight depression. The catalysts are generally based on chromium or noble metals (Pt) and their effectiveness must be periodically restored by means of a regeneration step in which the coke formed during the reaction is burnt. Numerous plant solutions can be used for the dehydrogenation comprising fixed bed reactors (adiabatic or isotherms), mobile bed or fluid bed reactors; the procedure to be used for supplying the heat necessary for the reaction (external heating or catalyst used as thermal carrier) obviously depends on the type of reactor adopted.

The butadiene formed in the dehydrogenation is selectively hydrogenated by the use of traditional catalysts based on supported noble metals, to linear butenes before the conversion steps. In this step, using a suitable catalyst, it is also possible to partially hydro-isomerize 1-butene to 2-butenes; this favours the production of a better quality of the product in the subsequent alkylation step and even if to a lesser degree, in the dimerization step with respect to the few isobutene/n-butenes co-dimers formed.

Dimerization

The dimerization of isobutene can be carried out either batchwise, in semi-continuous or in continuous, either in gas-solid phase or in liquid phase, generally at temperatures ranging from 50 to 300° C. and at atmospheric pressure or at pressures which are such as to keep the reagents in liquid phase, if desired. The catalysts which can be used for this reaction are the following: acids such as phosphoric acid, generally supported on a solid (for example kieselguhr), cation exchange acid resins, liquid acids such as $H_2SO_4$ or sulfonic acid derivatives, silico-aluminas, mixed oxides, zeolites, fluorinated or chlorinated aluminas, etc.

The main problem of dimerization, which has hindered its industrial development, is the difficulty in controlling the reaction rate; the high activity of all these catalytic species together with the difficulty in controlling the temperature in the reactor makes it extremely difficult to succeed in limiting the addition reactions of isobutene to the growing chains and consequently to obtain a high quality product characterized by a high selectivity to dimers.

In the dimerization reaction there is in fact the formation of excessive percentages of heavy oligomers such as trimers (selectivity of 15–60%) and tetramers (selectivity of 2–10%) of isobutene. Tetramers are completely outside the gasoline fraction as they are too high-boiling and therefore represent a net loss in yield to gasoline; as far as trimers are concerned (or their hydrogenated derivatives), it is preferable to greatly reduce their concentration as their boiling point (170–180° C.) is at the limit of future specifications on the final point of reformulated gasolines.

To enable a higher quality product to be obtained by reaching greater selectivities (dimer content>80% by weight) it is possible to use different solutions which are able to influence the catalytic activity and therefore control the reaction rate.

Oxygenated compounds can be used (tertiary alcohol and/or alkyl ether and/or primary alcohol) in a sub-stoichiometric quantity with respect to the isobutene fed in the charge using tubular and/or adiabatic reactors (IT-MI99/A001765 of Aug. 5, 1999).

Tertiary alcohols can be used (such as terbutyl alcohol) in a sub-stoichiometric quantity with respect to the isobutene fed in the charge using tubular and/or adiabatic reactors (IT-MI94/A001089 of May 27, 1994).

Alternatively, it is possible to suitably modify the charge by mixing fresh charge with at least a part of the hydrocarbon stream obtained after the separation of the product, in order to optimize the isobutene content (<20% by weight) and use a linear olefin/isobutene ratio higher than 3. In this case the use of a tubular reactor is fundamental for obtaining high selectivities (owing to the lower conditioning power of olefins with respect to oxygenated products), which allows optimum temperature control in the reactor, removing the heat as it is generated along the catalytic bed (IT-MI2000/A001166 of May 26, 2000).

Operating under these conditions, it is therefore possible to favour the dimerization of isobutene or isobutene/n-butene co-dimerizations, with respect to oligomerization, and avoid the activation of oligomerization-polymerization reactions of linear butenes which are favoured at high temperatures.

For all of these solutions, the range of process conditions, operating in liquid phase, includes a wide variety of operating conditions which are described hereunder.

The pressure is preferably super-atmospheric to keep the reagents in liquid phase, generally below 5 MPa, more preferably between 0.2 and 2.5 MPa. The reaction temperature preferably ranges from 30 to 120° C.

The feeding space velocities of the hydrocarbon streams should be preferably less than 60 $h^{-1}$, more preferably from 1 to 40 $h^{-1}$. Macro-latticed sulfonated resins, such as for example Amberlyst 15 and Amberlyst 35 produced by Rohm & Haas, are preferred catalysts.

The dimerization product is then preferably hydrogenated to give a completely saturated end-product, with a high octane number and low sensitivity. The hydrogenation can be carried out with conventional methods such as those described for example in F. Asinger, "Mono-olefins: Chemistry and Technology", Pergamon Press, Oxford, page 455.

As an example, Table 1 indicates the octane numbers and relative boiling points of some of the products obtained by the dimerization of isobutene.

TABLE 1

| PRODUCT | RON | MON | b.p. (° C.) |
|---|---|---|---|
| Diisobutenes | 100 | 89 | 100–105 |
| Iso-octane | 100 | 100 | 99 |
| Tri-isobutylenes | 100 | 89 | 175–185 |
| Hydrogenated tri-isobutylenes | 101 | 102 | 170–180 |

If for market reasons it is possible to even temporarily produce MTBE, isobutene can be converted to MTBE, either totally according to the classical etherification process, or partially by means of an etherification/dimerization process to give a mixture of MTBE and Iso-octene (mixture consisting of Di and Tri-isobutylenes) then hydrogenated to Iso-octane (IT-MI 95/A001140 of Jun. 1, 1995). In this latter case the MTBE and Iso-octene are separated before the hydrogenation of the latter.

Alkylation

Alkylation is a refinery process which consists in the formation of highly branched paraffins, with a high octane number, by the catalytic reaction of isobutane with light olefins such as propylene, butenes and amylenes; typical catalysts are mineral acids such as hydrofluoric or sulfuric acid. When butenes are used as olefinic charge, the more the production can be directed towards the formation of trimethylpentanes rather than dimethylhexanes or methylheptanes, the better the result will be.

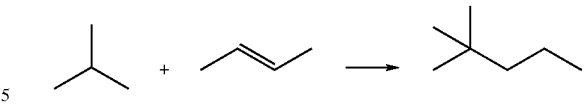

To obtain a high quality alkylated product, it is also necessary to minimize the oligomerization reactions of the olefin and high isobutane/olefin ratios much therefore be adopted: slightly higher than 10 in the HF process, a little less in that using $H_2SO_4$.

From the point of view of product quality, the alkylated product is a hydrocarbon component with a high Research octane number (RON) and has an extremely high Motor octane number (MON). Furthermore, it does not contain aromatics, sulfur or olefins, it respects the boiling range specifications and has a low volatility: it therefore has all the basic requisites for being an ideal component for environmentally more compatible reformulated gasolines.

The alkylation process is applied on a wide scale: in 1999 about 65 million tons of alkylated products were produced in the world. As far as the type of technology is concerned, about 60% of plants use HF and the remaining 40% $H_2SO_4$.

Another positive aspect of alkylation is that it succeeds in activating, by reaction in liquid phase catalyzed by strong acids, isoparaffinic hydrocarbons (which bind themselves to the olefins) thus ensuring higher productivities.

The following table indicates the octane numbers of alkylated products obtained from various olefins.

| INDUSTRIAL ALKYLATION PROCESSES PRODUCT QUALITY (octane number, ON) | | |
|---|---|---|
| Olefin | ON ($H_2SO_4$) | ON (HF) |
| Propylene | 90–92 | 91–93 |
| 2-butenes | 96–98 | 96–98 |
| 1-butene | 96–98 | 87–89 |
| Iso-butene | 87–89 | 93–95 |
| Pentenes | 91–92 | <90 |

From an environmental point of view, both $H_2SO_4$ and HF are strong acids, classified among dangerous substances, owing to their corrosive liquid nature. In the case, however, of discharge into the atmosphere due to an occasional accident, HF which is extremely volatile, forms a cloud of toxic vapors, whereas $H_2SO_4$ remains liquid and is therefore easier to treat. It should be pointed out on the other hand that the handling of enormous volumes of $H_2SO_4$ in routine operations, the disposal of its by-products and transporting of the acid for its recovery, analogously represent a great risk to the environment.

As a result of these problems, since the end of the eighties' there has been a wide interest in the development of alternative technologies which are more sustainable from an environmental point of view.

Alternative processes with solid acid catalysts are under study but their commercial applicability has not yet been demonstrated (Oil & Gas Journal, Sep. 9, 1996, 56). Some of them however are very close to commercial demonstration (S. M. Black, C. D. Gosling, K. Z. Steiglder, D. J. Shields, NPRA Annual Meeting 2000, San Antonio, Mar. 26–28, 2000, AM 00–20; S. I. Hommeltoft, L. Jorgensen, Erdól Erdgas Kohle, 115, (1998), 248).

A simplified process scheme is indicated in FIG. 1 enclosed to provide a clearer illustration of the present invention.

In order to feed the dehydrogenation section with the most suitable n-butane/isobutane ratio, a part, i.e. stream (2) of the total feeding of field butanes (1) is sent together with the stream of n-butane (21) leaving the bottom of the deisobutanating unit (DIB) to the skeleton isomerization section (ISOM); a stream of hydrogen (22) coming from an optional hydrogen purification section (HRU) is also sent to this section to suppress the polymerization reactions of the olefins formed as reaction intermediates.

The effluent (5) from the isomerization section is joined to the remaining part of the charge (3) and sent to the dehydrogenation section (DEHYDRO). The hydrogen produced during the dehydrogenation can be used, depending on the degree of purity required, as such in the subsequent hydrogenation steps or it can be sent to a purification section (HRU) and onwards, or used in the hydrogenation steps (streams 23 and 24) or destined for other uses (stream 25).

The $C_4$ products leaving the dehydrogenation (8) are then sent to the selective hydrogenation plant (HYDROG BTD) where the butadiene is converted to linear butenes. The mixture leaving this section (9) (mainly consisting of isobutane, n-butane, n-butenes and isobutene) is fed to the first conversion section (CONV_1) in which the isobutene is dimerized (and/or optionally etherified to MTBE) and the product obtained is subsequently hydrogenated (by means of stream 24) to give a mixture (11) mainly consisting of Iso-octane (selectivity 80–85% by weight) if the dimerization reaction alone is used, or of mixtures with a varying Iso-octane/MTBE content if there is also an etherification contribution to the isobutene conversion. The stream (12) containing linear olefins, which are not converted (or are only partially converted to a lesser degree of 5–10%) in this section, is then preferably joined to the isobutane (18) coming from the bottom of the depropanizing column (DEP) so as to have a correct ratio of saturated products/olefins, and sent to the alkylation section (CONV_2).

An alternative, not shown in the FIGURE, consists in totally or partially recycling the isobutane (18) to the first conversion section (CONV_1) and/or to the selective hydrogenation (HYDROG BTD).

In the alkylation, all the linear olefins react with the isobutane to form the alkylated product (14) whereas the $C_4$ paraffins (15) are sent to the deisobutanizing column (DIB) to separate the n-butane/isobutane. The n-butane stream (19) is recovered from the bottom of the column and is send back to the isomerization process (possible impurities present in the stream can be flushed by means of line 20). It should be noted that, for the sake of simplicity, the column in which the alkylated product is separated from the $C_4$ stream has been omitted.

A stream (16) is recovered from the head and is sent to the depropanizing column at whose head light products are obtained (17) and from the bottom of which isobutane (18) is recovered and sent to the alkylation section.

EXAMPLE 1

This example illustrates the use of the process of the present invention without however limiting its scope. The relative quantities of the products (Iso-octane and alkylated product) can in fact be varied in relation to the running conditions of the dehydrogenation section.

In the case of a feeding flow-rate of 665,000 t/year of field butanes (stream 1 of FIG. 1) having the following composition:

| Component | weight % |
|---|---|
| $C_3$ hydrocarbons | 2.4 |
| Isobutane | 20.1 |
| n-butane | 76.0 |
| $C_5$ hydrocarbons | 1.5 | and with the plant configuration indicated in FIG. 1, it would be possible to produce 205,120 t/year of Iso-octane (stream 11) and 357,580 t/year of alkylated product (stream 14) having the following properties:

| Properties | Iso-octane | Alkylated product |
|---|---|---|
| RON | 100 | 96 |
| MON | 100 | 93 |
| RVP, psi | 1.7 | 2.6 |
| Density, g/ml | 0.72 | 0.7 |

What is claimed is:

1. The process for the production of hydrocarbons with a high octane number starting from a mixture comprising n-butane and isobutane, comprising:
    a) feeding a part of the mixture comprising n-butane and isobutane a stream of hydrogen and a stream consisting of recycled n-butane, to a skeleton isomerization section, wherein said n-butane is isomerized;
    b) joining the product leaving the skeleton isomerization section with the remaining part of the mixture comprising n-butane and isobutane and sending the mixture thus obtained to a dehydrogenation section of paraffins;
    c) sending the stream leaving the dehydrogenation to a selective hydrogenation of butadiene;
    d) sending the stream leaving the selective hydrogenation section to a first conversion section in which the isobutene is reacted by dimerization separating the dimerized product from the non-reacted $C_4$ hydrocarbon stream, which comprises isobutane, n-butane and linear butenes, and subjecting said product to hydrogenation, thus providing a hydrocarbon stream comprising iso-octane;
    e) sending the $C_4$ hydrocarbon stream leaving the first conversion section, to a second conversion section in which all the linear butenes are reacted by alkylation with isobutane obtaining a stream of saturated hydrocarbons;
    f) sending the non-reacted butanes in the second conversion section to a first separation column (deisobutanizing column) from whose head a stream comprising propane and isobutane is recovered and from whose bottom n-butane is recovered to be recycled to the skeleton isomerization section;
    g) sending the stream at the head of the first separation column (deisobutanizing column) to a second separation column (depropanizing column) from whose head the light products are recovered and from whose bottom the isobutane is recovered, which is recycled to the second conversion section and/or to the first conversion section and/or to the selective hydrogenation section.

2. The process according to claim 1, wherein the mixture comprising n-butane and isobutane is a mixture of field butanes.

3. The process according to claim 1, wherein the isobutane recovered from the bottom of the second separation column (depropanizing column) is sent to the second conversion section.

4. The process according to claim 1, wherein the mixture comprising n-butane and isobutane have an n-butane/isobutane ratio ranging from 1/5 to 5/1.

5. The process according to claim 4, wherein the mixture comprising n-butane and isobutane have an n-butane/isobutane ratio ranging from 1/1 to 5/1.

* * * * *